United States Patent [19]
Cox et al.

[11] Patent Number: 6,029,079
[45] Date of Patent: Feb. 22, 2000

[54] EVALUATED TELETHERAPY SOURCE LIBRARY

[75] Inventors: Lawrence J. Cox, Los Alamos, N.Mex.; Alexis E. Schach Von Wittenau, Livermore, Calif.

[73] Assignee: Regents of the University of California, Oakland, Calif.

[21] Appl. No.: 09/082,511

[22] Filed: May 21, 1998

Related U.S. Application Data

[60] Provisional application No. 60/047,434, May 23, 1997.

[51] Int. Cl.$^7$ ........................................ A61N 5/10
[52] U.S. Cl. ............................................... 600/407
[58] Field of Search ................... 600/407, 408, 600/409, 410

[56] References Cited

U.S. PATENT DOCUMENTS

| | | | |
|---|---|---|---|
| 5,341,292 | 8/1994 | Zamenhof | 600/410 |
| 5,841,288 | 11/1998 | Meaney et al. | 600/407 |
| 5,870,697 | 2/1999 | Chandler et al. | 600/410 |

*Primary Examiner*—Scott M. Getzow
*Attorney, Agent, or Firm*—John P. Wooldridge

[57] ABSTRACT

The Evaluated Teletherapy Source Library (ETSL) is a system of hardware and software that provides for maintenance of a library of useful phase space descriptions (PSDs) of teletherapy sources used in radiation therapy for cancer treatment. The PSDs are designed to be used by PEREGRINE, the all-particle Monte Carlo dose calculation system. ETSL also stores other relevant information such as monitor unit factors (MUFs) for use with the PSDs, results of PEREGRINE calculations using the PSDs, clinical calibration measurements, and geometry descriptions sufficient for calculational purposes. Not all of this information is directly needed by PEREGRINE. It also is capable of acting as a repository for the Monte Carlo simulation history files from which the generic PSDs are derived.

14 Claims, 9 Drawing Sheets

| Manufacturer Model Configuration | Subdirectory Structure | | | |
|---|---|---|---|---|
| Varian Clinac 2100C X 6MV | Physical Geometry | Positions of Beam modifiers | | |
| | | Construction of wedges, etc. | | |
| | Simulation Based Entry (SBE) | Geometry of Simulation | | |
| | | Monte Carlo Histories from Simulation | | |
| | | PSD derived from histories | | |
| | | Monitor Unit Factor (MUF) | | |
| | | PEREGRINE Calculations using PSD | | |
| | Standard Entry (SE) | SE geometry modifications | | |
| | | SE measurements | | |
| | | SE PSD fit parameters | | |
| | | SE MUF | | |
| | | SE PSD calculations | | |
| | Clinical Entries (CE) | Site 1 | Date 1 | Site geometry constraints or modifications from standard |
| | | | | Site measurements |
| | | | | Site PSD fit parameters |
| | | | | Site MUF |
| | | | | Site calculations |
| | | | Date 2 | ... |
| | | Site 2 | Date 1 | ... |
| Varian Clinac 2100C X 15MV | ... | ... | | |

Table 1

| Bit | Meaning |
|---|---|
| 2 | target |
| 3 | target backing (variance reduction is done here) |
| 4 | vacuum after target |
| 5 | Primary Collimator Aperture (truncated cone of air) |
| 6 | Primary Collimator (cylinder with above cone missing) |
| 7 | Flattening filter (partially fills #5) |
| Monitor Chamber | |
| 8 | MC top iron |
| 9 | MC top air |
| 10 | MC middle iron |
| 11 | MC bottom air |
| 12 | MC bottom iron |
| 13-27 | Post monitor objects: Jaws, air etc. |
| 28 | Flag implying that the particle has NOT been Russian rouletted |
| 29 | Flag implying that the particle HAS been Russian rou letted |
| 30, 31 | Charge Bits (0,1)=e-; (1,0)=e+; (1,1) = photon |

Table 2

| Description | Bit | Events | Weight | Weight % | cm | Spot Radius |
|---|---|---|---|---|---|---|
| Target | 2 | 2793524 | 17769947 | 72.3 | 0.23 cm | 0.1 cm |
| Target Backing | 3 | 97498 | 840961 | 3.4 | 0.44 | |
| Post Target Vacuum | 4 | 68 | 491 | 0.002 | | |
| Primary Collimator Aperture | 5 | 535 | 3028 | 0.01 | | |
| Primary Collimator Metal | 6 | 82587 | 819192 | 3.3 | 5.68 | |
| Flattening Filter | 7 | 1087911 | 5022504 | 20.4 | 12.13 | 4.0 |
| Monitor Top Iron | 8 | 20016 | 120573 | 0.5 | | |
| Monitor Top Air | 9 | 4 | 31 | 0.0001 | | |
| All other structures | 10-27 | 0 | 0 | 0 | | |

Table 3

Table 5

| Case | | |
|---|---|---|
| 1 | < 0 | < 0 |
| 2 | < 0 | > 0 |
| 3 | > 0 | > 0 |
| 4 | > 0 | < 0 |

Table 4

| Field Size (cm x cm) | Array Dimensions | | | Side Lengths [cm] (Voxel Sizes [cm]) | | | Beam Orientation | Data to Extract (x,y,z ranges) |
|---|---|---|---|---|---|---|---|---|
| | $N_x$ | $N_y$ | $N_z$ | $L_x$ | $L_y$ | $L_z$ | | |
| 10x10 'A' | 15 | 210 | 15 | 15 (1.0) | 21 (0.1) | 15 (1.0) | SSD = 100 cm<br>Collimator: 0°<br>Gantry: 180°<br>Couch: 0° | DD = {D(8,1:210,8)}<br>$D_{max}$ = D(8,??,8)<br>Beam Normalization (from info file) |
| 10x10 'B' | 150 | 70 | 15 | 15 (0.1) | 21 (0.3) | 15 (1.0) | SSD = 100 cm<br>Collimator: 0°<br>Gantry: 180°<br>Couch: 0° | $P_{5x}$ = {D(1:150,16,8)}<br>$P_{20x}$ = {D(1:150,60,8)} |
| 10x10 'C' | 150 | 70 | 15 | 15 (0.1) | 21 (0.3) | 15 (1.0) | SSD = 100 cm<br>Collimator: 90°<br>Gantry: 180°<br>Couch: 0° | $P_{5y}$ = {D(1:150,16,8)}<br>$P_{20y}$ = {D(1:150,60,8)} |
| 2x2 | 41 | 210 | 41 | 4.1 (0.1) | 21 (0.1) | 4.1 (0.1) | SSD = 100 cm<br>Collimator: 0°<br>Gantry: 180°<br>Couch: 0° | DD = {D(21,1:210,21)}<br>$P_{5x}$ = {D(1:41,50,21)}<br>$P_{20x}$ = {D(1:41,200,21)}<br>$P_{5y}$ = {D(21,50,1:41)}<br>$P_{20y}$ = {D(21,200,1:41)} |
| 4x4A | 81 | 210 | 21 | 8.1 (0.1) | 21 (0.1) | 8.4 (0.4) | SSD = 100 cm<br>Collimator: 0°<br>Gantry: 180°<br>Couch: 0° | DD = {D(41,1:210,11)}<br>$P_{5x}$ = {D(1:81,50,11)}<br>$P_{20x}$ = {D(1:81,200,11)} |
| 4x4B | 81 | 210 | 21 | 8.1 (0.1) | 21 (0.1) | 8.4 (0.4) | SSD = 100 cm<br>Collimator: 90°<br>Gantry: 180°<br>Couch: 0° | $P_{5y}$ = {D(1:81,50,11)}<br>$P_{20y}$ = {D(1:81,200,11)} |
| 40x40 'A' | 251 | 70 | 25 | 50.2 (0.2) | 21 (0.3) | 50 (2.0) | SSD = 100 cm<br>Collimator: 0°<br>Gantry: 180°<br>Couch: 0° | DD = {D(126,1:70,13)}<br>$P_{5x}$ = {D(1:251,16,13)}<br>$P_{20x}$ = {D(1:251,60,13)} |
| 40x40 'B' | 251 | 70 | 25 | 50.2 (0.2) | 21 (0.3) | 50 (2.0) | SSD = 100 cm<br>Collimator: 90°<br>Gantry: 180°<br>Couch: 0° | $P_{5y}$ = {D(1:251,16,13)}<br>$P_{20y}$ = {D(1:251,60,13)} |

Table 4

EVALUATED TELETHERAPY SOURCE LIBRARY

This application claims benefit of Provisional Application Ser. No. 60/047,434, May 23, 1997.

The United States Government has rights in this invention pursuant to Contract No. W-7405-ENG48 between the United States Department of Energy and the University of California for the operation of Lawrence Livermore National Laboratory.

RELATED APPLICATIONS

Copending U.S. patent application Ser. No. 08/610,917, titled "Calculation of Radiation Therapy Dose Using All Particle Monte Carlo Transport" is fully incorporated herein by reference.

BACKGROUND OF THE INVENTION

Field of the Invention

The present invention relates to radiation therapy, and more specifically, it relates to a system of software and data files that describe radiation sources for use in PEREGRINE, a Monte Carlo radiation therapy dose calculation code.

Description of Related Art

Currently in the United States, radiation therapy is used to treat about 60% of all cancer patients. Since radiation therapy targets specific areas of the body, improvement in radiation treatment techniques has the potential to reduce both mortality and morbidity in a large number of patients.

The radiation source may be may be in the form of external beams of ionizing particles or radioactive sources internal to the patient. External beams are usually produced by machines acting as particle accelerators. The beam delivery system consists of the radiation source, which is mounted on a gantry which can rotate about a 360° arc around the patient. Each beam is shaped by a rotatable collimator. The patient lies on a rotatable table. The gantry and table both rotate about a single isocenter.

External beam radiation therapy is performed with several types of ionizing radiation. Approximately 80% of patients are treated with photons, ranging in maximum energy from 250 keV to 25 MeV. The balance are treated primarily with electrons with energies from 4 to 25 MeV. In addition, there are several fast neutron and proton therapy facilities which have treated thousands of patients worldwide. Fast neutron therapy is performed with neutron energies up to 70 MeV, while proton therapy is performed with proton energies ranging from about 50 to 250 MeV. Boron neutron capture therapy is conducted with thermal and epithermal neutron sources. Most internal radioactive sources irradiate the patient with photons, although some sources emit low energy electrons.

The effects of ionizing radiation on the body are quantified as radiation dose. Absorbed radiation dose is defined as the ratio of energy deposited to unit mass of tissue. Because tumors and sensitive structures are often located in close proximity, accuracy in the calculation of dose distributions is critically important. The goal of radiation therapy is to deliver a lethal dose to the tumor while maintaining an acceptable dose level in surrounding sensitive structures. This goal is achieved by computer-aided planning of the radiation treatments to be delivered. The treatment planning process consists of characterizing the individual patient's anatomy (most often, this is done using a computed tomography (CT) scan), determining the shape, intensity, and positioning of radiation sources (the subject of the present invention), and calculating the distribution of absorbed radiation dose in the patient. Most current methods used to calculate dose in the body are based on dose measurements made in a water box. Heterogeneities such as bone and airways are treated in an approximate way or ignored altogether. Next to direct measurements, Monte Carlo transport is the most accurate method of determining dose distributions in heterogeneous media. In a Monte Carlo transport method, a computer is used to simulate the passage of particles through an object of interest.

SUMMARY OF THE INVENTION

It is an object of the present invention to provide a system of software and system files that describe radiation sources for use in PEREGRINE.

PEREGRINE is an all-particle, first-principles 3D Monte Carlo dose calculation system designed to serve as a dose calculation engine for clinical radiation therapy treatment planning (RTP) systems. By taking advantage of recent advances in low-cost computer commodity hardware, modern symmetric multiprocessor architectures and state-of-the-art Monte Carlo transport algorithms, PEREGRINE performs high-resolution, high accuracy, Monte Carlo RTP calculations in times that are reasonable for clinical use. Because of its speed and simple interface with conventional treatment planning systems, PEREGRINE brings Monte Carlo radiation transport calculations to the clinical RTP desktop environment. PEREGRINE is designed to calculate dose distributions for photon, electron, fast neutron and proton therapy.

The PEREGRINE Monte Carlo dose calculation process depends on four key elements: complete material composition description of the patient as a transport mesh, accurate characterization of the radiation source (the subject of the present invention), first-principles particle transport algorithms, and reliable, self-consistent particle-interaction databases (also an element of the present invention). PEREGRINE uses these elements to provide efficient, accurate Monte Carlo transport calculation for radiation therapy planning.

The patient transport mesh is a Cartesian map of material composition and density determined from the patient's CT scan. Each CT scan pixel is used to identify the atomic composition and density of a corresponding transport mesh voxel. Atomic composition is determined from CT threshold values set by the user or by default values based on user-specified CT numbers for air and water. The user also assigns materials and densities to the interior of contoured structures. If the user specifies a structure as the outer contour of the patient, PEREGRINE constructs a transport mesh that is limited to the maximum extent of that structure, and sets all voxels outside that structure to be air. This provides a simple method of subtracting the CT table from the calculation. The default resolution of the transport mesh is 1×1×3 mm, for small-volume areas such as the head and neck, or 2×2×10 mm, for large-volume treatment sites such as the chest and pelvis. The resolution can also be reduced from the CT scan resolution. For reduced-resolution voxels, material composition and density are determined as the average of all CT pixels that fall within the transport mesh voxel.

The PEREGRINE source model, designed to provide a compact, accurate representation of the radiation source, divides the beam-delivery system into two parts: an accelerator-specific upper portion and a treatment-specific lower part. The present invention relates to this source model. The accelerator-specific upper portion, consisting of the electron target, flattening filter, primary collimator and monitor chamber is precharacterized based on the machine vendor's model-specific information. These precharacterized sources are derived from Monte Carlo simulations from off-line Monte Carlo simulations using BEAM and MCNP4A, as described in copending U.S. patent application Ser. No. 08/610,917, which is fully incorporated herein by reference. Particle histories from off-line simulations are cast into multidimensional probability distributions, which are sampled during the PEREGRINE calculation. The photon beam is divided into one or more subsources of types: primary, scattered, and contaminant. Separating the source into subsources facilitates investigation of the contributions of each individual component. To ensure site-specific model accuracy, the installation procedures will consist of a limited number of beam description parameter adjustments, based on simple beam characterization measurements. The lower portion of the radiation source consists of treatment-specific beam modifiers such as collimators, apertures, blocks, and wedges. This portion is modeled explicitly during each PEREGRINE calculation. Particles are transported through this portion of the source using a streamlined transport scheme. Photons intersecting the collimator jaws are absorbed. Photons intersecting the block or wedge are tracked through the material using the same physical database and methods described below for patient transport. A need exists for a system of software and data files that describes radiation sources for use in PEREGRINE to handle access, modification (revision control) and use of the descriptions of clinical teletherapy radiation sources used in the treatment of cancer by radiation. The Evaluated Teletherapy Source Library (ETSL) provides such a system of hardware and software.

The ETSL is a computer code system that provides the following functions in an integrated software library:

It analyzes large Monte Carlo simulation history files of standard linear accelerators and generates compact, 9 dimensional (7 degrees of freedom) probability distribution functions (PDFs) describing the patient-independent radiation field for use in Monte Carlo dose calculation. This reduces storage requirements and allows subsequent calculations to select an arbitrary number of uncorrelated samples from the PDF.

The 7 degrees of freedom in the PDF are (i) spectral energy, (ii) energy fluence (sample weight), (iii) and (iv) two positional degrees of freedom (radius on the BDP and radius on VSP), (v) an angular degree of freedom (azimuthal angle on VSP), (vi) radiation type ((discrete), including photons (x-rays), electrons, neutrons and protons), and (vii) component of origin information (discrete) including E.G.: target, flattening filter and primary collimator.

Included in the analysis are the eventual effects of some patient-dependent beam modifiers to provide data necessary for highly efficient sampling. (This means that a precalculation is made of the effects of the collimator jaws on the shadowing of the beam definition plane to eliminate large portions of PDF from consideration at run time.)

The ETSL assembles a treatment device description (TDD) from a radiation field PDF and from engineering details of the patient dependent beam modifiers specific to each clinical installation. It adjusts the PDFs using 7 linear parameters and clinical measurements to give absolute calibration of the radiation field for each clinical installation. The Global Monitor Unit Factor is the global normalization constant that defines the dose/MU for a 40×40 field. The Monitor Chamber Parameter including radius and position information. These parameters are used to adjust the monitor unit factor to account for deviations in the calculated output factors from the measured values. The Global and Radial Energy Scale Factor are multipliers on the energy axis of beam-definition-plane energy spectra. The Radial Fluence Scale Factor is a multiplier on the energy fluence that is proportional to the radius on the beam definition plane.

The ETSL provides storage, access and maintenance routines for use in calibration and dose calculation. It provides sampling methods for efficiently selecting random samples that accurately reproduce the original simulations (for unadjusted PDFs) or the actual radiation fields used in treatment (for adjusted PDFs). The ETSL provides formats and access to the clinical data used in calibration for quality assurance and is extensible to any radiation beam type, including x-rays, electrons, protons, neutrons and heavy ions. Radiation types can be mixed in a single TDD to account for radiation field contaminant such as electrons in an x-ray beam (or vice versa), or neutrons in a proton beam.

Using the Monte Carlo transport method, PEREGRINE tracks all photons, electrons, positrons and their daughter products through the transport mesh until they reach a specified minimum tracking energy or leave the patient transport mesh. Developing good statistics requires tracking millions of representative particles (histories) through the patient transport mesh. During the simulation, PEREGRINE records energy deposited at each interaction, which builds up a map of energy deposited in the transport mesh. After the Monte Carlo process is finished, a dose map is created by dividing the total energy deposited in each voxel by its material mass. PEREGRINE transports photons through the body using the standard analog method. Woodcock or delta-scattering is used to efficiently track particles through the transport mesh. All photons below 0.1 keV energy are absorbed locally. PEREGRINE transports electrons and positrons using a class II condensed-history scheme. This procedure groups soft collisions with small energy losses or deflections, but simulates directly those major or catastrophic events in which the energy or deflection angle is changed by more than a preset threshold. Delta-ray and bremsstrahlung production are modeled discretely for energy transfers >200 keV. PEREGRINE uses the Goudsmit Saunderson theory of multiple elastic electron/positron scattering. Pathlength corrections described are used to account for the effect of multiple scattering on the actual distance traveled by the electron or positron. A minimum electron/positron transport energy is assigned to each transport voxel based on range rejection. The range-rejection minimum energy corresponds to the minimum electron/positron range required to traverse 20% of the minimum zone dimension, with range determined as the minimum range calculated for that zone plus all directly adjacent zones. Two 511 keV photons are created at the end of each positron range. The direction of the first photon is chosen randomly, while the second is set to 180° opposed to the first.

The accuracy of Monte Carlo dose calculations depends on the availability of reliable, physically-consistent physical databases. For photon/electron/positron transport, PEREGRINE relies on the Lawrence Livermore National Laboratory Evaluated Physical Database, combined with stopping powers supplied by the National Institute of Standards and Technology.

PEREGRINE accounts for photon interactions via the photoelectric effect, incoherent/coherent photon scattering, and pair production. All photon cross sections used by PEREGRINE are derived from the Lawrence Livemore National Laboratory Evaluated Photon Data Library (EPDL). EPDL data are taken from a variety of sources that have been selected for accuracy and consistency over a wide range of photon energies (10-eV-100-MeV) for all elements.

At low incident photon energies (<0.1 MeV for tissue components, <1 MeV for high-Z materials such as lead and tungsten), the photoelectric effect is the dominant absorption mechanism. The cross sections contained in PEREGRINE were obtained by direct evaluation of the relativistic S-matrix in a screened central potential. These cross sections accurately describe ionization from electrons bound in isolated atoms and provide predictions at the percent level for compounds where the K and L shells are well-represented by atomic orbitals. For most elements, at energies typical of those encountered for clinical photon beams, Compton scattering is the most important process in the photon-atom interaction. The Compton scattering cross sections used in PEREGRINE are obtained in the incoherent scattering factor approximation. This approximation includes screening effects. Relativistic effects enter through use of the Klein-Nishina cross section. Coherent scattering does not contribute significantly to the total photon-atom interaction cross section for most radiation therapy applications. However, these cross sections are still modeled, and were obtained under similar assumptions to those for incoherent scattering. At very high incident photon energies (>30 MeV for tissue components, >5 MeV for high-Z materials such as lead and tungsten), the dominant photon interaction mechanism is pair production. The cross sections for pair and triplet production used by PEREGRINE include Coulomb and screening effects and radiative corrections.

PEREGRINE accounts for the effects of large-angle elastic scattering (delta-ray production) and bremsstrahlung production on an event-by-event basis. All other energy-loss mechanisms are accounted for through continuous-slowing-down-approximation (CSDA) energy loss.

Moller (Bhabha) scattering is the ionization of an atom by an electron (positron). Moller and Bhabha cross sections and sampling methods follow those given by Messel and Crawford. The threshold for these processes in PEREGRINE is set so that the ejected electron kinetic energy is >200 keV.

Bremsstrahlung cross sections contained in PEREGRINE are derived from the LLNL Evaluated Electron Data Library (EEDL). These cross sections were determined by interpolating between the relativistic S-matrix data available up to 2 MeV, and the Bethe-Heitler result, expected to be valid above 50 MeV. Bremsstrahlung cross sections are processed to reflect a bremsstrahlung photon energy cutoff of 200 keV. During transport, PEREGRINE uses restricted collision and radiative stopping powers, which exclude energy lost due to Moller/Bhabha events with energy transfers >200 keV and bremsstrahlung events with energy transfers >200 keV. Restricted collision stopping powers are calculated. Restricted radiative stopping powers are calculated by subtracting the total energy transferred to the bremsstrahlung photon per distance, as determined from the bremsstrahlung cross section data.

The accuracy of PEREGRINE transport calculations has been demonstrated by benchmarking PEREGRINE against a wide range of measurements and well-established Monte Carlo codes such as EGS4 and MCNP. PEREGRiNE benchmarks can be divided into two classes: the first set of comparisons validates the transport algorithms used to calculate dose in the patient; the second set of comparisons tests the accuracy of radiation source characterization and implementation, as well as transport through the patient. The second set is also useful for assessing the benefits of Monte Carlo calculations over current dose calculation algorithms.

FIG. 1 shows a comparison of PEREGRINE calculations with measurements for (a) a 1-MeV electron beam incident on carbon and for (b) a 22.5-MeV electron beam incident on water. Results are normalized to a relative maximum dose of 1.0. Distance is expressed in terms of practical range.

PEREGRINE results have been compared with independent measurements and calculations for simple electron and photon sources. FIG. 1(A) compares PEREGRINE depth dose calculations for a 1-MeV electron pencil beam incident normal on a semi-infinite carbon slab with calorimeter measurements. FIG. 1(B) compares PEREGRINE depth dose calculations for a 22.5-MeV electron pencil beam incident on a water slab measurements. Measurements were made for a broad beam with minimum scattering material, but with a correction for beam divergence. Calculations and measurements are normalized to maximum dose. Depths are given in fractions of the practical range. Calculations and measurements are in excellent agreement.

FIGS. 2A and B illustrate the results of comparing PEREGRINE calculations with EGS4 for a 6 MV photon pencil beam incident normal to the center of a broad slab phantom. FIG. 2(A) compares PEREGRINE and EGS4 calculations for water-air-water slabs; 2(B) compares results for water-iron-water slabs. EGS4 calculations were completed with bremsstrahlung photon (AP) and delta-ray production (AE) cutoff energies of 10 keV and 521 keV, respectively. Results for both codes are in excellent agreement.

In addition to validating the accuracy of PEREGRINE Monte Carlo transport algorithms, PEREGRINE calculations have been compared with a wide variety of clinical measurements for homogeneous and heterogeneous phantoms. Benchmarking against clinical measurements verities the accuracy of radiation source characterization and implementation, as well as transport through the patient.

FIG. 3 demonstrates the accuracy of PEREGRINE calculations for water phantoms measurements made on a Varian 2100C 6-MV photon beam. PEREGRINE dose calculations were compared with ion chamber measurements in a water phantom for 2×2, 10×10, and 20×20-cm fields. Profile and depth dose comparisons are shown. Profiles are normalized to measured or calculated depth dose values for each depth. PEREGRINE calculations were completed using energy and angular distributions derived from a manufacturer-specified description of the Varian 2100C accelerator head. The only free parameter in the accelerator source characterization was the electron spot size. These calculations were made with a version of PEREGRINE that included full photon transport in the collimator jaws. In similar comparisons for the version of PEREGRINE that assumes that all photons intersecting the collimator jaws are absorbed, measurements were made using an air-equivalent ion chamber with an outer diameter of 6 mm, wall thickness of 0.4 mm, and active length of 3.3 mm. All measurements were smoothed.

FIG. 4 illustrates the excellent agreement between PEREGRINE calculations and preliminary radiochromic film measurements for heterogeneous phantoms. The phantom was irradiated at 100-cm SSD by a 10×10-cm beam. The solid water phantom had a 3-cm-wide-by-3-cm-thick square air heterogeneity (infinitely long on the gantry-target axis) centered along the central axis of the beam, with its top surface at 1.5-cm depth. The film was positioned perpendicular to the beam at 6-cm depth in the solid water phantom.

The Peregrine Dose Calculation Engine (PDCE) combines the hardware, software, and networking components required to add this single-unit desktop design to any radiation treatment planning (RTP) system via a simple network connection, much like a file server. The PDCE implements the PEREGRINE physics software under control of a modern, multithreaded operating system that supports the use of server-class, symmetric multiprocessing (SMP) microprocessors. The software design efficiently distributes the calculations for the problem so that dose is calculated by many microprocessors in parallel. The design is scaleable in a master-slave configuration such that a number of slave main-boards can be configured to compute in parallel, while result accumulation and communications are controlled by a single master board.

The PDCE is constructed from off-the-shelf components originally developed for file- and Internet-server applications. The design combines a configurable number of motherboards interconnected by an internal high-speed network. Each main board supports up to four PentiumPro CPUS with supporting memory and peripherals. The use of commodity hardware and a flexible hardware architecture allows the engine to be configured at a number of cost/performance points. The design supports hardware upgrades for increased capability in microprocessor hardware technology.

The PDCE can be optionally equipped with a display and supporting software to provide real-time visualization of the PEREGRINE Monte Carlo dose calculation while it computes. The display illustrates the effects of multiple beams and facilitates an early assessment of the plan's efficacy. Additional display capabilities are being developed to quantitatively monitor the progress of the dose calculation.

Once installed, PEREGRINE will operate as a dose calculation engine for a RTP system, calculating dose distributions for individual patient treatment plans. The RTP communicates with PEREGRINE via the AAPM Specifications for Treatment Planning Data Exchange, augmented by a small number of extensions, which provide additional beam- and patient-description data needed for Monte Carlo calculations. Once the treatment plan description is sent, the PDCE authenticates and checks files, computes the dose, and returns the results in new files for display and manipulation on the RTP system.

The PEREGRINE dose calculation system is designed to provide high resolution, high-accuracy dose calculations for clinical radiation therapy planning. PEREGRINE can be economically integrated into existing RTP systems as an "invisible" dose computer, providing state-of-the-art capability to all clinics. The availability of such calculations could improve effectiveness of radiation therapy by providing accurate radiation treatment planning for every patient, facilitating accurate clinical trials and reliable implementation of these results throughout the medical community, providing accurate estimates of required doses for tumor control and normal tissue tolerance, and aiding in advancing the field of radiation oncology.

BRIEF DESCRIPTION OF THE TABLES

Figure 1B:
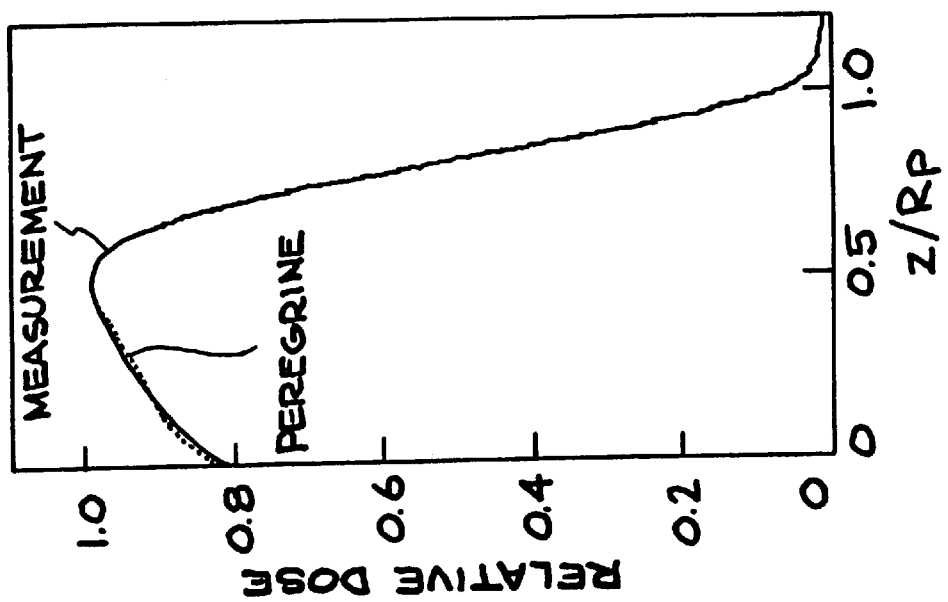
FIG. 1(B) compares PEREGRINE depth dose calculations for a 22.5-MeV electron pencil beam incident on a water slab measurements.
Figure 1A:
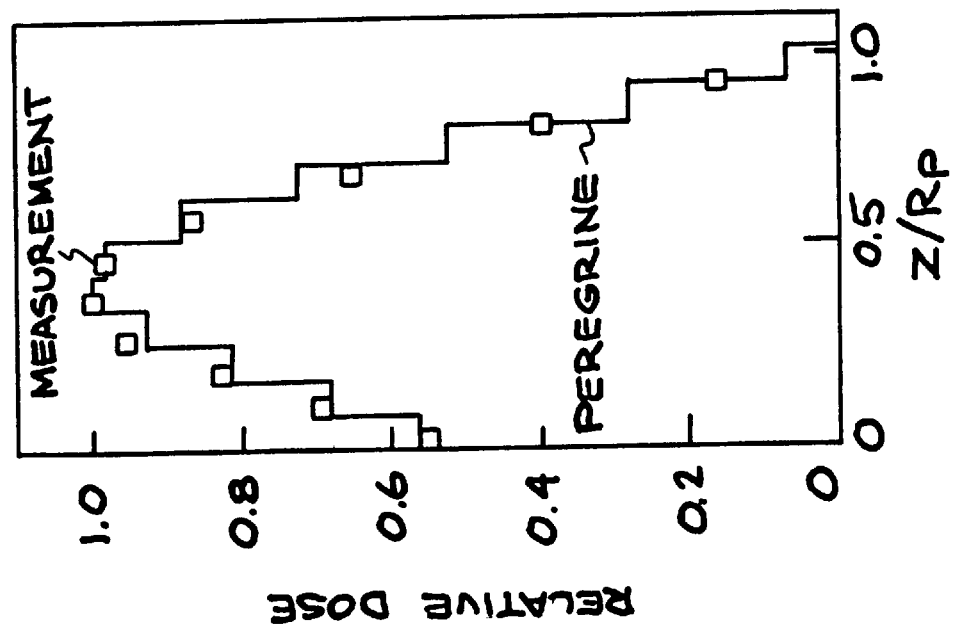
FIG. 1(A) compares PEREGRINE depth dose calculations for a 1-MeV electron pencil beam incident normal on a semi-infinite carbon slab with calorimeter measurements.
Figure 2A:
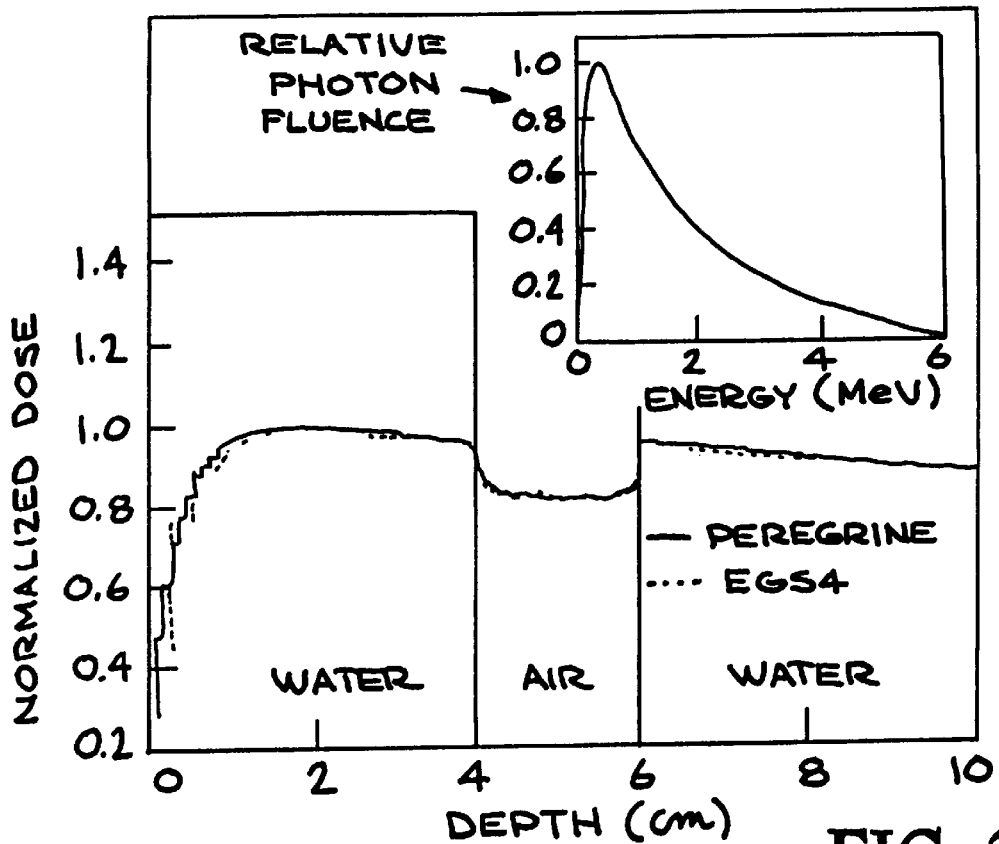
FIG. 2(A) compares PEREGRINE and EGS4 calculations for water-air-water slabs.
Figure 2B:
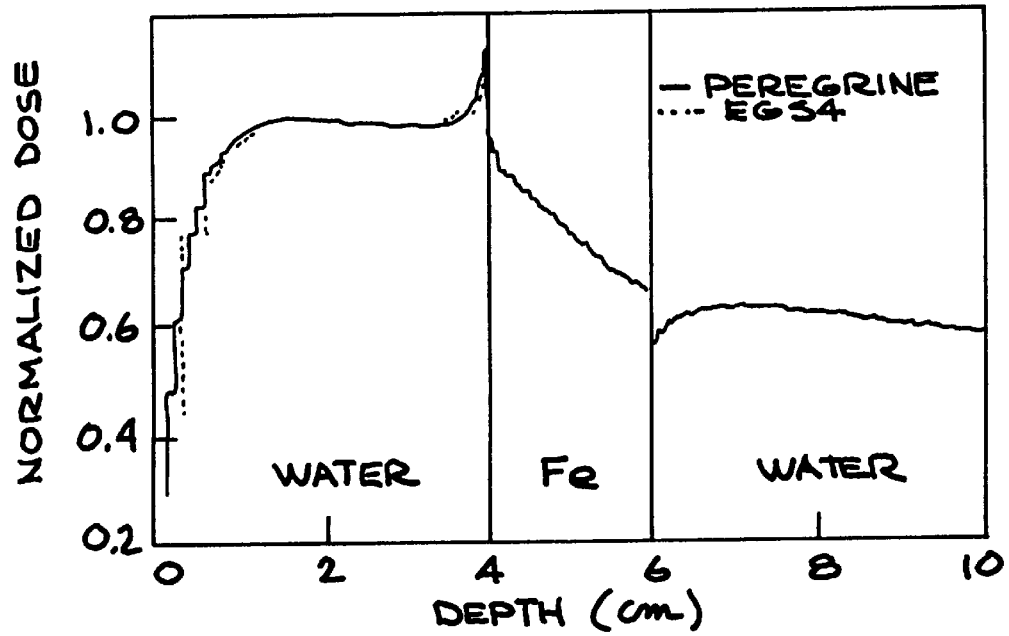
FIG. 2(B) compares results for water-iron-water slabs.
Figure 3:
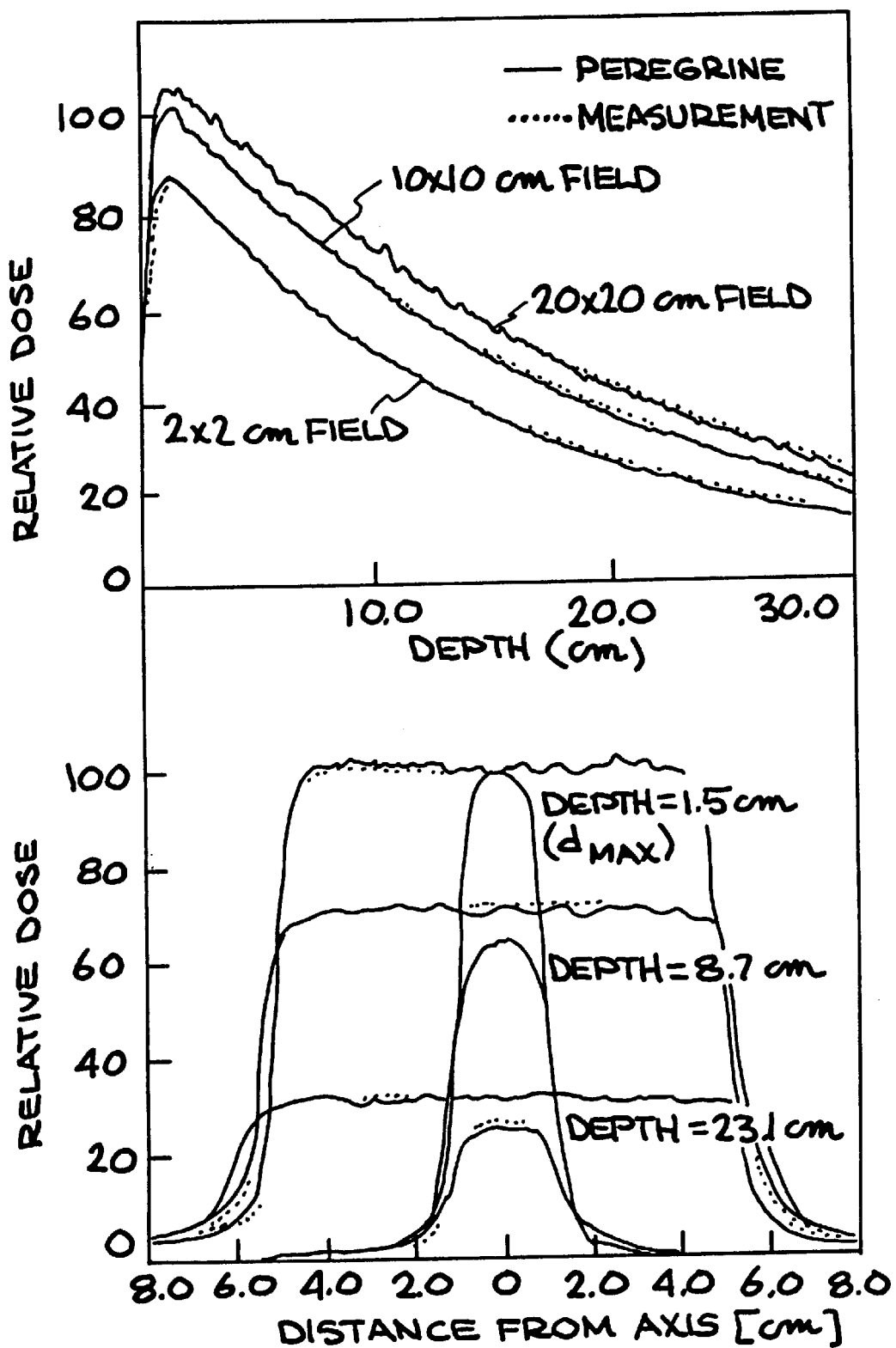
FIG. 3 demonstrates the accuracy of PEREGRINE calculations for water phantoms measurements made on a Varian 2100C 6-MV photon beam.
Figure 4:
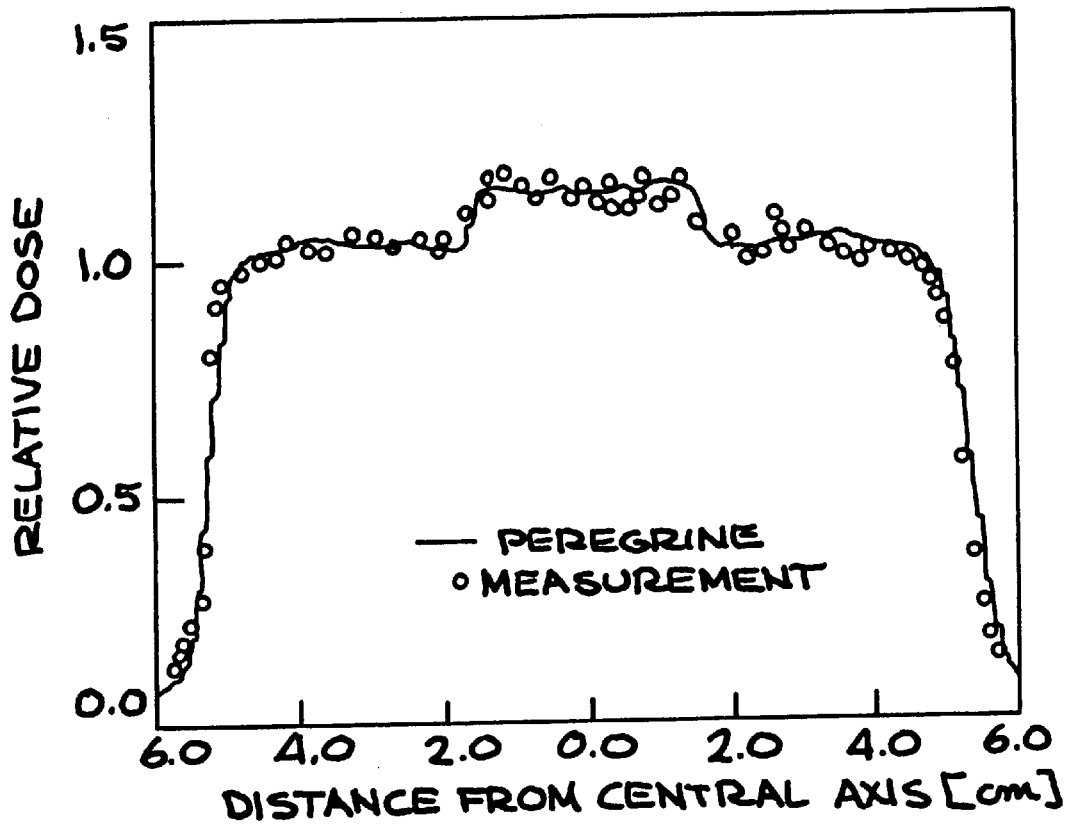
FIG. 4 illustrates the excellent agreement between PEREGRINE calculations and preliminary radiochromic film measurements for heterogeneous phantoms.

Table 1 lists examples of the types of contents that each different entry type will require.

Table 2 provides the meaning of the various history bits.

Table 3 lists the number and weight of last interactions, object by object, for photons in the MSKCC Varian Clinac 2100C×6MV history file.

Table 4 contains specifications for the various phantoms to calculate for each new PSD.

Table 5 lists the variables needed for the four cases of a ray passing through the two z-planes that define a model of a jaw.

DETAILED DESCRIPTION OF THE INVENTION

I. What PEREGRINE Needs from an External Source Description

In addition to the radiation type, PEREGRINE needs to know the following quantities in the beam coordinate system for each history to be tracked:

(x,y,z): the starting coordinates;

(u,v,w): the initial direction cosines with respect to (x,y,z) respectively;

(E): the sample energy; and (W): the relative sample weight.

These quantities typically are provided for a few million particle histories from a Monte Carlo beam simulation of a given machine type. Different accelerators of the same type are tuned differently and result in slightly different radiation distributions as evidenced by differences in depth-dose and profile measurements for otherwise identical fields. Hence, a history tape derived for one location may not be directly applicable to another similar machine. Given a sufficient number of events, PEREGRINE can read particle descriptions directly from a history file. This would, of course, preserve all features of the simulation. However, a typical PEREGRINE calculation involves tens of millions of individual unique source samples. It is not practical to store enough uncorrelated events on disk or tape for every single operating mode of each accelerator type. It has been suggested that a history tape of a few million events could be used over and over, reusing only the events that reach the transport mesh For small fields, the selected events would be a small fraction of a history file and would lead to poor illumination statistics-which would not benefit from perturbations of the random number sequence-giving, perhaps a severe limit on the ultimately achievable accuracy.

Therefore, such Monte Carlo simulations must be analyzed and characterized into a form from which PER- EGRINE can sample infinitely many individual uncorrelated samples. That characterization can then also be optimized to a local instance of a particular accelerator type using a set of local measurements by adjusting a few parameters.

II. Library Design

II.A Implementation Levels and Access

This teletherapy source library has two levels of implementation.

The highest level-the Master Library-contains all available information about all analyzed instances of each different device configuration. A device configuration is a specific manufacturer's model number operating at a given energy and may include special beam modifiers such as a multi-leaf collimator or dynamic wedge. This is the level in which details of the simulations and the histories are stored.

The other level is the Clinical Installation Library. This implementation is a subset of the Master Library containing only the information specific to the particular clinical site. Other uses for this level are to supply data on the analysis of their hardware to the manufacturers while not revealing potentially proprietary information about other manufacturers devices.

Both of these library implementations have two access levels. The highest access level allows users to add new entries and modify current ones (to a limited extent). The second access level allows read only access to users of the library. An example of the read-only access level is PEREGRINE's use of Phase Space Description (PSD) files. Phase Space Description is used interchangeably with Treatment Device Description (TDD). Examination of library contents is another example. Second level access users will have read-only access to all library information. Access limitations can be enforced by directory permissions and group ownership or by password protection.

III. Library Entry Types, Contents and Structure

Generation of library entries is based on Monte Carlo simulations of beam delivery systems combined with clinical measurements. An entry in ETSL will consist of at least the following information: a phase space description, the associated monitor unit factor or factors, and PEREGRINE calculations using the PSD. See Table 1 for an example of the types of contents that each different entry type will require. Entries will fall into one of at least three distinct categories:

III.A. Simulation Based

Simulation Based Entries (SBEs) will not rely on measurements directly. These entries will be derived from Monte Carlo simulations of teletherapy beam delivery heads above the first patient modifier. No adjustments will be made to match clinical measurements. Instead they will represent the best that current Monte Carlo simulation codes can do based on the quality of the physics and structure of the beam head. However, adjustments designed to match calculations of depth-dose and profiles from the original simulation may be included, if those calculations are available. If this is done, then the results of those calculations will be added to the library entry. A standard set of PEREGRINE calculations will be done using the SBE-PSD and stored with the details of the simulation in the library entry.

III.B. Standard

This is intended to be a special instance of an evaluated PSD where adjustments are made to the SBE to bring PEREGRINE calculations into agreement with the measurements. An evaluated phase space description is an analyzed Monte Carlo simulation adjusted to match clinical measurements. Using the expertise of our MEDPAC members, we will identify and establish collaborations with institutions best able to deliver a comprehensive, accurate set of dose measurements for each beamline configuration added to ETSL to use for making adjustments to the SBE-PSD. Measurements, adjusted PSD files, PEREGRINE calculations, identity of the creator and date of creation will be stored in the library entry as the standard for the specific configuration. One possible source of these measurements is from the manufacturers' commissioning measurements.

III.C Clinical

These dated evaluated entries will be the workhorses of the library, being what PEREGRINE will generally use for clinical dose calculations. A clinical entry (CE) will be a PSD modified to result in PEREGRINE calculations that match a provided set of site specific clinical calibration measurements. A certain set of measurements-not necessarily as comprehensive as the Standard set-will be required from participating institutions and compared to the Standard Measurements. If the site measurements are within tolerance (TBD), then an CE-PSD will be generated from the measurements and the SBE-PSD. These entries are intended to be the workhorses in the clinic and can be updated whenever a periodic calibration shows significant deviation (to be determined (TBD)) from a stored CE based PEREGRINE calculations. The clinical measurements, evaluated PSD, PEREGRINE calculations, identity of the evaluator and date of evaluation will be stored in the library IV. Site Evaluation Software Clinical Site Adjustment The most important aspect of source description is the ability to match measurements from, and therefore accurately calculate dose for, a given clinic. Since specific installations of similar linacs can have subtle differences in head construction and electron beam characteristics, as well as different modifier options and site calibrations methods, some site adjustment of the generic source description will be necessary for each installation.

To facilitate this adjustment, certain information about the installation site is required. Measurements of output factors, open field depth dose, open field profiles and wedge factors are necessary. A description of the monitor unit calibration configuration and convention is needed to determine the proper global normalization constant. Physical descriptions of modifier options, such as wedges and blocks, are also necessary. For wedges, the physical wedge profile, the material (alloy) and density of the wedge and tray, and the axial location of the wedge tray are needed. For blocks, the block thickness, material and density, and the location of the block tray must be pro-vided. Any other special modifiers must also be described if they are to be used in PEREGRINE calculations.

Given access to this data, a simple, few-parameter fit allows the adjustment of the generic machine description Three typically used parameters are the maximum photon energy, the radial fluence of the point component, and the shape of the point-component virtual source.

The Clinical Evaluation Software package will adjust certain parameters to bring PEREGRINE calculations into agreement with routine clinical calibration measurements. It will act as a driver for PEREGRINE, requesting a series of calculations using a modified PSD. The tools will be built in "tool" modules that access necessary data using standard structures as defined for use with the NCI Tools with data extensions as needed by our specific tools.

IV.A. Clinical Evaluation Software Tools

IV.A(i) Comparison Tool

The Clinical Comparison Software Tool will compare a set of PEREGRINE calculations to clinical measurements. It will access an index of available PEREGRINE calculations and clinical measurements. Mismatches between the two indexes will be reported to the user and will imply missing data or calculations. Available comparisons between matching data sets will include:

1) Simple over plotting of calculations and measurements;
2) Percent difference plots;
3) Figures of merit (FOM); FWHM, $D_{max}$, Depth dose slope, . . .
4) $x^2$/DOF
5) Normalilzation factors
6) Comparison to stored tolerances

IV.A(ii) Adjustment Tool

The Clinical Adjustment Software Tool will be used to make adjustments to a PSD to bring PEREGRINE calculations into better agreement with clinical measurements. The steps in making an adjustment include:

1) Verifying that provided measurements are within allowed tolerances for the given configuration;

2) Estimating corrections to PSD parameters using stored standard PEREGRINE calculations. This requires defining the parameters and their allowed ranges;

3) Running the series of PEREGRINE calculations and extracting the necessary data;

4) Iterating until within calibration tolerances or to some maximum number of iterations; and 5) If calibration tolerances cannot be achieved within the maximum number of iterations, not allowing generation of a CE-PSD, but reporting back the best fit parameters and comparisons; or 6) If calibration tolerances are reached, querying the evaluator about the subjective adequacy of the fit and allowing the generation of a CE-PSD on their request.

IV.B. Identification of Tuning Parameters

The most important task of this project is to identify the features of a PSD that need to be varied to bring PEREGRINE calculations into agreement with clinical measurements. When such features are identified, a parameterization of the PSD will be developed. It will be necessary to obtain multiple sets of good clinical measurements on a representative device to allow sufficient exploration of the parameter space. Some possibilities for adjustable features and proposed parameters are give in this section.

IV.B.(i) Peak Energy

The maximum energy of the beam may be useful as a parameter to adjust depth-dose penetration. The energy spectral shape would be specified on a unit base and the value between 0 and 1 selected would be a fraction of the maximum energy. With off axis measurements of depth-dose, it may be possible to consider different factors for different radii to improve fit. The need for this added flexibility will have to be determined from having two or more comprehensive measurements on the same configuration either at different sites or different rooms of the same site.

IV.B.(i) Field Width

The beam width at isocenter is measured clinically from 50% dose level to 50% dose level (FWHM). PEREGRINE currently uses a geometric field width specified at axis from plan-specified jaw positions. The transverse physical position of the jaws is determined by assuming a perfect point source and back-projecting to the physical jaw positions. This gives rise to PEREGRINE fields that are wider than measurements since the geometric field border is not at the half-max level. The FWHM is slightly narrower than the geometric field due to the finite size of the primary source component.

It may be sufficient to provide an additive offset for all fields since the shadowing effect of the jaw edges will be relatively independent of the opening. Different offsets for the top and bottom sets of jaws may be needed due to the different aspect ratios of the actual jaw positions for a given field. This will have to be explored by obtaining accurate profiles in both transverse directions for various field sizes.

IV.B.(i) Relative Radial Energy Fluence

Horns on profiles can vary from machine to machine of the same type due, for example, to on-site adjustments to beam flatness. To adjust for this, it may be sufficient to allow evaluation software to vary the radial energy fluence of the primary and/or scattered components. One possible approach would be to determine a polynomial function which would be used as a multiplier on the SBE radial fluence distributions.

V. Library Access Software

The access software is correlated to the PEREGRINE dose calculation system development to enable PEREGRINE to directly access ETSL for source information. Other tools will also have to be developed to allow access to the stored measurements and calculations.

V.A. PEREGRINE Direct Access

A query request will be provided that will allow PEREGRINE users to select from the available list of evaluated teletherapy sources. Depending on the implementation and level of access, the user may also access a limited list of CE-PSDs for use with PEREGRINE. Protection against use of unavailable or unauthorized PSD entries will be provided either by ETSL or the RTP system.

V.B. Tools for Viewing Library Entries

Viewing tools and/or data extraction tools allow all users to access measurements and calculations from all available library entries for viewing and comparison purposes.

V.C Tools for Updating Library

All update options to ETSL will be restricted by password or group limited access to prevent corruption of library entries or improper use of incomplete entries.

V.C.(i). Certifying Entries

ETSL entries intended for use in clinical comparisons will require certification by the evaluator that the entry is complete and accurate enough for clinical use. Different level of applicability will be allowed to be designated by the evaluator. These will include 1) treatment planning application, 2) retrospective clinical comparison application, 3) research application. Other application levels may be added.

V.C.(ii). Adding New Entries

New entry additions will need to be checked for completeness. Incomplete entries will be stored marked as pending/incomplete and will be unavailable for PEREGRINE calculations.

V.C.(iii). Completing Pending Entries

Update access to incomplete entries will be limited to the originator. Other qualified users will be allowed to copy and complete such entries and will then become the official evaluator for the new entry.

V.C(iv). Modifying Complete Entries

Modification of evaluated entries will not be allowed. To change an entry because it is invalidated in some way, it must be copied and then deleted or archived. After modification, it is stored as a new entry.

V.C.(v). Deleting Outdated Entries

Provisions will be made for completely removing library entries. A record of the deletion, comments and identity of the operator will be kept.

V.C.(vi) Archiving Outdated Entries

Provisions will be made for removing outdated entries from the active list. Such entries will still be accessible for comparison purposes to active entries but will not be accessible by PEREGRINE. Reactivation of archived entries will not be allowed, but copying and re-evaluation will be. Such re-evaluations will constitute new library entries.

VI. Analysis of Monte Carlo Simulation History Files

The following discussion is based on analysis of simulations done at Memorial Sloan Kettering using their code McRad or our codes BEAM and MCNP. The simulations analyzed so far are for the Varian Clinac 600C (2100C) at 6MV and 15MV. A binary history file(s) is received that gives (x,y,u,v,E) coordinates for a few million simulation histories tallied on an exit plane at z=100 cm from the physical electron target.

Each event also provides a 32 bit history record specifying the charge (particle type), importance (1 or 10), and interaction history. Table 2 shows the meaning of the various history bits. This information is essential in our analysis. A history bit is set if the particle had an interaction or was originated in the corresponding physical element. With this information, the simulation histories can be subdivided into different components. MSKCC is only modeling the patient independent portions of the beam, therefore we should-and do-find that none of the history bits are set after bit 12.

To date, all simulations considered have been modeled as fully cylindrically symmetric above the patient modifiers. The analysis assumes and relies on this symmetry.

VIA. Separation into Subsources

By using the history information, two distinct categories of simulation events from accelerator simulations can easily be identified and analyzed: direct and scattered. A majority of events and total energy consists of events that had no interactions after the target backing. These direct events can be analyzed and easily cast into a finite sized point source model with a high degree of accuracy. The remainder of events have one or more interactions in the primary collimator, flattening filter or monitor chamber and are referred to herein as scattered events. Table 3 shows the number and weight of last interactions, object by object, for photons in the MSKCC Varian Clinac 2100C×6MV history file. A history weight, W, refers to the number of real particles that the history represents. It is extracted from the history bits.

The MSKCC history files give (x0,y0,u,v,E,W) at $z_0$=100 for each event. The variables u and v are the x and y direction cosines, respectively. E is the particle energy and W is the history weight. The product EW is the total history energy. Equation 1 gives (x,y) as a function of u,v,z. Using these forms, the value $z_{min}$ that yields the minimum radius is given by Equation 2. The best location for characterization of a given component is selected by finding the mean value of $z_{min}$ from all events assigned to that component. Table 2 also shows and spot size for each component when its events are mapped to that location.

$$x = x_0 + (z - 100)u/w \qquad \text{(Eq. 1)}$$
$$y = y_0 + (z - 100)v/w$$
$$w = \sqrt{1 - u^2 - v^2}$$

$$z_{min} = 100 - \frac{w(ux + vy)}{1 - w^2} \qquad \text{(Eq. 2)}$$

VI.B. Direct or Point Source Characterization

The current model for describing the photon phase space for a direct component of an accelerator based photon source is described here. This type of source is referred to as a point source of photons.

For a point source component, we define a Virtual Source Plane (VSP) at $Z_{vsp}=(z_{min})$ and a Beam Definition Plane (BDP) just in front of the first patient modifier-usually the upper jaws-at z=$z_{BDP}$. The two spatial distributions at these locations can be used to sample the initial position and direction of Monte Carlo source events in PEREGRINE. Sampling methods are described in Section IX.

The VSP spatial distribution is determined by backtracking each event to z=$z_{VSP}$ using Equations 1 and 2. The events are used to generate a radial probability distribution at the VSP. An idealized point source—one in which all events effectively originate from a single point—can be made by confining the VSP distribution to a single point at (0,0,$z_{vsp}$).

The BDP spatial distribution is determined in the same way using z=$z_{BDP}$. For point sources, however, the BDP distribution is stored in the form of a relative fluence function of radius instead of a probability function. A perfectly flat energy fluence can be generated by specifying a constant radial fluence function over the entire defined area of the BDP.

The energy of point source phase space particles is specified on the BDP on a series of annular radial tiles. A different probability distribution in energy is created for each BDP tile. The radial span of the BDP tiles should match the span of the BDP fluence function. Tiles cannot overlap, but an open core or between tile gaps are acceptable under the current definition.

Two methods of generating the probability and fluence functions are discussed in Sections VI.D and VI.E.

VI.C. Scattered or Plane Source Characterization

The other currently supported type of source component is referred to as a plane source. The plane source PSD definition does not require a virtual source plane. A plane source BDP is defined at $z_{BDP}=(Z_{min})$ averaged over all selected events. At this location, a radial probability distribution is generated. The energy, z-direction cosine (w) and transverse radial direction cosine ($\cos\phi_r$) are specified on a series of annular tiles. For each annulus, we generate an independent probability distribution for these three variables.

Figure 5:
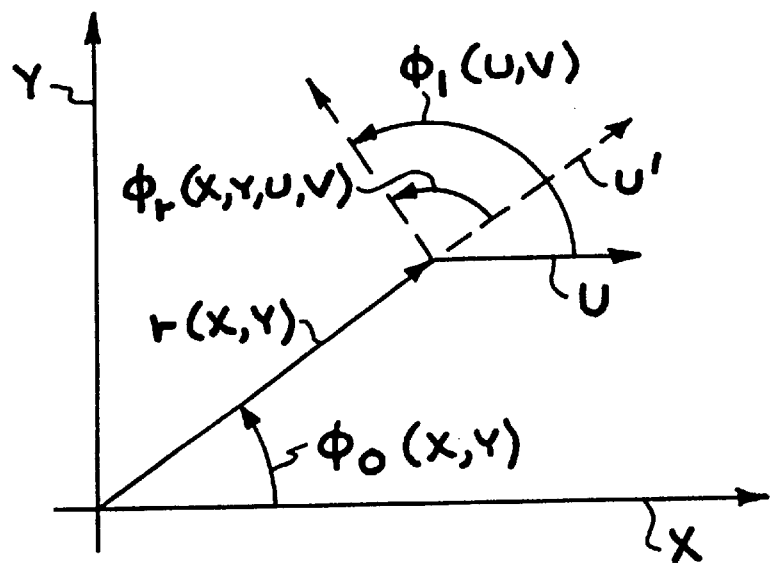
FIG. 5 shows the geometric relationships between the various coordinates in the transverse plane used in PSD generation. Equation 3 gives the functional relationships.

Currently, these three distributions are independently generated without consideration of correlations. There is some indication in the simulations obtained so far that correlations between angle and energy as a function of radius may be important to accurately represent the simulation phase space in a compact PSD. FIG. 5 shows the geometric relationships between the various coordinates in the transverse plane used in PSD generation. Equation 3 gives the functional relationships.

$r = \sqrt{x^2 + y^2}$, radial position; (Eq. 3)

$\phi_0 = \text{atan}(y/x)$, position azimuth;

$\phi_1 = \text{atan}(v/u)$, direction azimuth;

$\phi_r = \phi_1 - \phi_0 \in \{-\pi, \pi\}$, radial direction azimuth;

VI.D. Particle Count Based Probability Distributions

The method of extracting a probability distribution from a simulation history file is straightforward and is the same for all independent variable types: radius, energy, or angle. Equation 4 states the standard summation rule defining a normalized histogram with independent variable boundaries.

$$\frac{d}{dx}P(x_{j+1/2}) = \frac{1}{W_{total}(X_j - X_{j-1})}\sum_i W_i, \quad \text{(Eq. 4)}$$

for all $i \in \{i \mid X_{j-1} < x_i < X_j\}$ $W_i$ and $W_{total}$ are the individual event and component total particle weights given in the simulation history file. When defining radial tile energy and angle distributions, only histories in the selected annulus are included in the sum.

A count based fluence function needed for a point source BDP is defined slightly differently. For a radial function, Equation 4 has units of [#/cm]. To get [#/cm²], instead of dividing by bin width, it is necessary to divide by annulus area, $A_j = \pi(R_j^2 - R_{j-1}^2) = 2\pi R_{j+1/2}\Delta R_j$. Furthermore, to get a relative fluence, whose average value is one, a factor of $A_{total}$ is needed. Assuming no gaps and no open center, $A_{total} = \pi R_N^2$. Then the summation rule for a unit average fluence function is given in Equation 5.

$$\frac{d}{r dr}P(R_{j+1/2}) = \frac{A_{total}}{A_j W_{total}}\sum_i W_i, \quad \text{(Eq. 5)}$$

for all $i \in \{i \mid R_{j-1} < r_i < R_j\}$.

VI.E. Energy Based Probability and Fluence Distributions

Accelerator based photon sources are tuned using filters to generate a flat energy fluence distribution transverse to the beam direction at the nominal isocenter. This suggests that the quantity we should strive to preserve in our PSD development is the nature of the simulated and measured energy fluence (MeV/cm²). This is in contrast to basing the distributions on photon fluence [#/cm²] as described in Section VI.D. It is only necessary to include the energy in the summations of Equations 4 and 5 and to divide by the total component energy, $E_{total}$, instead of $W_{total}$. The revised forms are in Equations 6 and 7 for energy based probability and relative fluence respectively.

$$\frac{d}{dx}P(x_{j+1/2}) = \frac{1}{E_{total}(X_j - X_{j-1})}\sum_i E_i W_i, \quad \text{(Eq. 6)}$$

for all $i \in \{i \mid X_{j-1} < x_i < X_j\}$ $$\frac{d}{r dr}P(R_{j+1/2}) = \frac{A_{total}}{A_j E_{total}}\sum_i E_i W_i, \quad \text{(Eq. 7)}$$

for all $i \in \{i \mid R_{j-1} < r_i < R_j\}$.

VI.F. History File Generation for Direct Use in PEREGRINE

Besides the two different source types defined above, PEREGRIN can also use a history file of events taken directly from a simulation. Certain assumptions are made regarding the simulation and the events are cast into a minimum form.

Our current knowledge of the construction of beam heads above the beam modifiers is that the geometries above the first set of jaws is cylindrically symmetric to a high degree. Because of this, we make the assumption that the underlying function of a history file is also azimuthally symmetric about the beam axis. Hence, any given simulation history is still a valid history after an arbitrary azimuthal rotation of the coordinates and direction cosines about the beam axis.

With this assumption, each history event can be described by four values, $z_t z_j z_b x x_{tp} x_{bp} x x_{tj}, x_{bj} x' s \Delta x_t$ and $\Delta x_b$. Using Equation 1, each history is moved to the beam definition plane giving coordinates $(x_{bdp}, y_{bdp}, u, v)$. The history is rotated to lie on the x axis which also rotates the x and y direction cosines which transforms the coordinates to $(r_{bdp}, 0, u_r, v_a)$ using Equation 8.

$$u_r = (u x_{bdp} + v y_{bdp})/r_{bdp}$$
$$v_a = (v x_{bdp} - u y_{bdp})/r_{bdp} \quad \text{(Eq. 8)}$$

To avoid possible ordering bias in the simulation file, events are selected randomly from the entire set and written into the PEREGRINE history file. For example, if there are 15 million (weighted) events in the original simulation history and 1 million (unit weight) events are wanted in the PEREGRINE history file, 1 million are selected randomly from the simulation file using a uniform random number selection. The weight of the simulation histories can vary and this is taken into account when deciding to keep or reject a given history. In the MSKCC simulations, the histories have either 1 or 10 weight. For the 10 weight histories, up to 10 identical events can be written to the file. Each of the ten is independently Russian-rouletted by the factor of 1:15 (in this example). The PEREGRINE history file is stored as a binary file comprised of records of 4 real numbers $z_t z_j z_b x x_{tp} x_{bp} x x_{tj}, x_{bj} x' s \Delta x_t$ and $\Delta x_b$. In this way, 1 million events occupies 16 MB on disk or in RAM. See Section IX.E for detail on how PEREGRINE uses these history files.

VII. Calculations for Verifying a PSD using PEREGRINE
VII.A. PEREGRINE Test Suite Driver A driver script will be developed that will execute a series of PEREGRINE calculations as read from a list using a single PSD. The script will be adapted for parallel execution of different calculations on multiple independent CPU platforms.

VII.B. Calculation List and Description

Table 4 contains specifications for the various phantoms to calculate for each new PSD. Notice that the phantoms are all constructed to have a voxel centered on the beam. This will allow extraction of the exact centerline dose without resorting to averaging. If more cross sectional area is ever desired for any of the calculations, voxel size can be increased.

VII.C. Extraction of PEREGRINE profiles

An extraction software tool that is list driven will be developed to automate extraction of profiles from PEREGRINE calculations. The data needed from the current list of calculations is also shown in Table 4.

VII.D. Format

The output format will be a multi-column, commented, ASCII file suitable for input into standard plotting packages. Wherever possible, similar measurements-such as x and y profiles at different depths—will be combined into a single file. Comment and information lines will be marked by a pound sign (#) in column 1. Data lines will have a blank in column 1.

The comment section of each file will identify the PSD, specify the phantom construction and beam angles, describe the beam geometry and state the PEREGRINE version & date. It will also describe the data as depthdose or profile, state the index ranges used for data extraction, the number of data columns, the number of data lines in the file and provide the factor used to convert to dose/MU. The last comment line before the data will be a row of column headings to identify each column.

For depthdose, three columns will be written: depth index(1:N); physical depth to center of voxel; and calculated dose per monitor unit. The units of dose will be cGray.

Since all of these PEREGRINE calculations are axisymmetric, profile data will be symmetrized about the axis and be reported in a six column format: index (0:N); off-axis distance (cm); $P_{5x}$; $P_{5y}$; $P_{20x}$; $P_{20y}$. The tabulated profile doses will be normalized to the dose per monitor unit factor determined from the 10×10 field calculation.

VIII.A Weighted Source Selection

Select the beam and subsource using a distribution based on the beam weights and subsource weights. To implement weighted source selection, we need to consider beam weights (MU*MU_FACTOR) and subsource weights. The number of sources is $N_{beam}*N_{subsrc}$ (if all beams have the same number of subsources). An alias sampling distribution is built using these values and source selection is be done with a call to ICHOICE.

Gain: Less rejection of scattered component photons leading to more efficient sampling. With no other changes a factor of 1.67 was realized for 10×10 fields and increasing for smaller fields due to higher rejection rate of scattered photons.

Con: Higher discrepancy between particle weights (~10× instead of ~2×). Discrepancy will increase with decreasing field size.

Con: Sampling is still based on pre-modifier ratios. A better scheme would somehow use post-modifier component ratios for sampling to further increase efficiency.

VIII.B. Point Source Jaw Margin Reduction

Reduce the margin on point source tracking to be the VSP width scaled by the ratio. For a 3 mm spot diameter this is reducing the jaw margin to 2 mm instead of 1 cm.

Gain: For a 10×10 field, the additional increase would be a factor of 1.42 for an overall factor of 2.37 speedup. Smaller fields would be even more efficient due to the ratio of the marginal area to the field area. For a 2×2 field, the ratio between marginal area to field area would be reduced by 15×. Even with elimination of plane source sampling (ignoring head scatter completely), the maximum speedup would be a factor of 3.3× for 2×2; 2.84× for 10×10; 1.1× for 40×40 fields.

Con: Less illumination of the penumbra areas by transmitted photons. Inadequate illumination for full transport model.

VIII.C. Reduction of Tracking through Jaws/Collimators (V961217)

By reducing the transport to ray tracing through the jaws/collimators, a factor of 1.08 was gained in the source particle generation.

Pro: Fast tracking.

Con: No inscatter or backscatter corrections to output factors and monitor units calculation.

VIII.D. Reduction of Scattered Component to Area of Primary Spot (in use for V961217)

The scattered photons from the simulations show a large spot size at the beam isocenter. By characterizing the scattered source from those photons that lie within the spotsize determined by the primary collimator, the wide angle photons that would not clear the jaws are eliminated. This is only a change to the machine file and requires no changes within PEREGRINE. Another factor of 1.09 is gained by using such a source.

Pro: Elimination of sampling of photons that would be killed by ray tracing.

Con: No obvious cons with ray tracing through jaws.

If we revert to a technique that allows scatter off of jaws, then the wide angle photons that may scatter back into the beam will not be included.

VIII.E. Weight Balancing by Scattered Photon Splitting (V961217)

The alias-antialias source sampling introduced a larger discrepancy in particle weights between the point source and scattered source components. There is the potential that high weight, rare events may lead to poor statistical convergence. I implemented what I call fraternal cloning of scattered photons that dear the jaws. Since the photon energy is not used in determining clearance of the jaws, it remains a free parameter. V961217 currently reuses the spatial and direction values for valid scattered photons and selects a unique energy for each reuse from the appropriate energy spectrum. The splitting factor, $N_n$, is defined by Equation 9 where $\overline{E_n}$ is the average photon energy of component n on axis and $f_n$ is its sample fraction. This value is calculated internally to PEREGRINE.

$$N_n = \text{int}\left(\frac{\overline{E_1}}{\overline{E_n}}\left(\frac{f_n}{f_1}\right) + 0.5\right) \tag{Eq. 9}$$

Pros: Weights are balanced to be all essentially constant only varying as the average energy varies with radius.

Pro: Speed Gain. By counting each successful scattered photon more than once, the overall efficiency is increased.

Con: The fraternal clones all start at the same place on the patient with different energies. This is still better than one large monoenergetic bundle. A spectrum of photons adding up to the same weight is laid down instead. This will be somewhat mitigated by blocks and/or wedges in which we to full transport. The different energies will be attenuated and scattered differently.

VIIIF. Plane Source Phase Space Preprocessing

Preprocess plane source phase space "cells" through jaws and blocks (attentuation only).

Gain: By eliminating all cells with no probability (95%+) and (in the presence of wedges) precalculating an average attentuation for remaining cells, plane source sampling would become 100% efficient. This would save all the time used in rejection and tracking of these particles through the patient modifiers.

Quantification of the actual savings would require an implementation.

Pro: By properly renormalizing the plane source component weight, particle weights could be made more uniform. This may reduce the variance of our dose calculation and therefore reduce the time to convergence.

Con: Significant memory usage even with elimination of blocked or low probability cells. There are approximately 4.9 million cells in a plane source phase space that need to be checked. 95% rejection would still leave 250000 cells to sample.

This only accounts for position and direction and ignores energy. If we include energy (which we would have to due to additionally preprocess wedges) another factor of $N_{energy}$ (50) would be applied to the number of cells needing to be checked.

Significant time will be added to the startup overhead.

IX. PSD Sampling Techniques for use in PEREGRINE

The generation of a PSD from a simulation history file is, of course, driven by the intended end use. This section discusses the current sampling and normalization techniques used in PEREGRINE. Since the final phase space description (PSD) of the teletherapy source also imposes restrictions on the sampling techniques, a detailed description of the intended sampling method for use in PEREGRINE—or any other Monte Carlo code that may use these sources—is given.

IX.A. Source and Subsource Selection

IXA.(i) Equiprobable Sampling with Weight Adjustment

As of Aug. 1, 1996, PEREGRINE was selecting a source/subsource by treating all defined sources as equally probable. Since weights between beams (sources) and the internal weights of the subsources within a beam can all be different, this method requires a weight adjustment to each sample generated. The sample weight for a selected subsource is calculated using Equation 10 with these variables: $W_{beam}$, the selected beam's importance; $N_{beam}$, the number of beams; $W_{comp}$, the internal weight fraction of the selected component; $N_{comp}$, the number of components in the selected beam; $N_{total}$, the total number of requested histories for the entire PEREGRINE calculation. See Section IX.B for a discussion of beam normalization and a definition of $W_{beam}$.

$$W_{st} = W_{beam} W_{comp} \frac{N_{beam} N_{comp}}{N_{total}} \quad \text{(Eq. 10)}$$

For example, consider a calculation requesting $10^6$ histories with one beam. If that beam has two subsources having weights of 85% and 15%, $W_{st}$ for the first component would be $W_{beam} * 1.7 \times 10^{-6}$. $W_{st}$ for the second component would be $W_{beam} * 3.0 \times 10^{-7}$. Due to differences in sampling techniques from type to type, to get the actual sample weight in units of moles or actual particles, it is necessary to apply additional scaling depending on the component type.

IXA.(ii). Component Weighted Sampling without need for Weight Adjustment

An alternative to the equiprobable source sampling is to base selection of a subsource on its share of the total source weights. A PDF can be assembled from the different beam and component weights. Then, a random lookup in that table delivers a source/subsource combination. The example given above would result in 85% of samples chosen directly chosen from the first component and 15% from the second. The values for Wst would constant across source samples but would still require scaling depending on the selected component's type. This method has been implemented in PGV1_961217.

IX.B. Beam Normalization and Monitor Units

The current beam normalization in PEREGRINE is based on a unit of energy. The variable $W_{beam}$ is in energy units. It can be thought of as the number of monitor units prescribed to the beam times the MeV per monitor unit for that beam's PSD. A monitor unit is clinically defined as the radiation "on time" to deliver 1 cGray at $D_{max}$ in water for a 10 by 10 field. It is essentially proportional to the amount of radiation delivered above patient modifiers. The exact position and structure of the water phantom and depth of measurement may vary from clinic to clinic. With this interpretation, lacking calibration of the global scale factor, one beam unit should produce one MeV of total energy. Since, PEREGRINE currently continues generating particles until the requested number of histories actually reaches the patient, the total energy is somewhat more that expected. Because of the current stop criteria in PEREGRINE, and since different components have different transmission through patient modifiers, the actual delivered energy and the total energy may both vary significantly from the expected total. What is presently preserved in the PEREGRINE model is the ratio between components in the total beam energy.

Absolute dose is determined clinically by the conversion from monitor units (MU) to measured dose per MU. One prevalent standard is to calibrate the monitor chamber to deliver 1.0 cGy/MU at $d_{max}$ on the central axis for a 10 by 10 open field. The beam normalization in PEREGRINE is based on total energy produced in the beam head before modifiers. PEREGRINE determines relative dose in the patient mesh by tracking individual photon histories. Photons are not explicitly tracked through the monitor, but instead are tallied to get the total sampled beam energy from all components. To obtain absolute dose for comparison to clinical measurements, a conversion between total beam energy and MU is required. This is done by calculating the dose in the calibration configuration and recording the necessary conversion factor between total beam energy and MU in the source description file.

PEREGRINE can calculate dose from multiple beam plans in a sin-gle calculation, if the weight (in MU) of each beam is specified in the plan. PEREGRINE maintains energy balance between the beams and components in the ratios given in the plan and source description by selecting histories from the beams at random, based on the partition of the total produced energy. The partitioning includes the MU for each beam, the MU factors in the source descriptions, and the component energy fractions in each source.

Besides accuracy in the description of the radiation field, efficiency (speed) is a critically important issue in delivering a practical Monte Carlo dose calculation. This component model is designed for efficient sampling. By defining the radiation fluence at the isocenter, the cropping effects of collimator jaws can be precalculated beam by beam at generation, eliminating the need to sample from large portions of the beam definition plane (BDP). For example, on a 10 by 10 field, confining the sampling area for the point component to that area—plus a margin to account for the virtual source plane (VSP) spot size—eliminates ~92% of the BDP from consideration. The transmission through the body of the jaw is ignored. For scattered components, a larger margin is used based on the extent and location of the VSP, but a significant portion of the BDP can still be ignored.

To preserve energy balance between the components and weight balance between the individual histories, component selection is based on a probability distribution that includes the beam weights, component energy fractions, and the BDP sample fractions. The initial values for x and y are chosen uniformly in the remaining rectangle on the BDP.

Internal to PEREGRINE, the weight of a selected history is considered to be a molar weight, not a measure of the total energy of the history. With this definition of the BDP and the selection process for x and y, the molar weight of a history is given by $$W = \frac{\phi(r)}{\langle E(r) \rangle}$$

where $\langle E(r) \rangle$ is the average photon energy at r(x,y). $\langle E(r) \rangle$ and $\phi(r)$ are obtained by linear interpolation from tabulated values. The selection of energy and VSP location are done directly from the associated probability distributions.

IX.C. Point Source Sampling

The components of a PSD for a point source are described in Section VI.B. When a point source component is selected, a Monte Carlo sample is selected from that information as follows:

1) A radius is chosen at $z_{vsp}$ from the VSP radial distribution;

2) $x_{vsp}$ and $y_{vsp}$ are selected uniformly from the circle at that radius;

3) At the BDP, $(x,y)_{bdp}$ are selected uniformly from a rectangle that represents the projection of the jaws (plus a fixed margin) onto the BDP. If the selected position results in a radius that is larger than the outer radius of the BDP, the sample is rejected as non-physical and is not recorded in any tally;

4) The initial unit direction vector (u,v,w) is defined by these two points: $(x,y,z)_{vsp}$ and $(x,y,z)_{bdp}$;

$$dl = \sqrt{\Delta x^2 + \Delta y^2 + \Delta z^2} \quad \text{(Eq. 11)}$$
$$u = \Delta x / dl, \quad v = \Delta y / dl, \quad w = \Delta z / dl$$

5) The relative energy fluence, $E_{flu}$, is looked up from the BDP relative fluence function using the selected radius, $r_{bdp}$ defined by $(x,y)_{bdp}$.

6) From $r_{bdp}$, a tile index is selected by linear area interpolation. Each tile distribution is treated as defining the distribution at the area center of the tile, $(R_J)$. For $(R_{J-1}) < r_{bdp} < (R_J)$, tile J is selected with probability $P_J$ as defined in Equation 12. Tile (J-1) is selected with probability $(1-P_J)$.

$$P_J = \frac{r_{bdp}^2 - R_{J-1}^2}{R_J^2 - R_{J-1}^2} \quad \text{(Eq. 12)}$$

The index (J=1) is used for $r_{bdp}<(R_1)$, and for $r_{bdp}>(R_N)$ the index (J=N) is used. Using this method removes the piecewise constancy of the tiles. The result is smooth variation essentially quadratically in radius.

7) A sample energy, $E_{samp}$, is selected from the probability distribution associated with the selected tile.

8) The sample weight is determined by $W_{st}E_{flu}/E_{samp}$. However, another factor must be applied since we did not select from the entire BDP but instead limited our selection to a rectangle describe in 3) above. This factor is the ratio of the energy fluence within the BDP selection rectangle to the total energy fluence on the BDP. This ratio is calculated analytically in PEREGRINE for each jaw setting by integrating the fluence function over the rectangle and dividing by the integral over the entire BDP. The subroutine RADINT.F does this integration. It is discussed in Section X.A(i).

The final result is a complete sample description at the BDP with the values (x, y, z, u, v, w, E, W)$_{bdp}$.

IX.D. Plane Source Sampling

The main difference between point source sampling and plane source sampling lies in the determination of the sample initial direction. The selection process is as follows:

1) A radius, $r_{bdp}$, on the BDP is selected from the BDP radial probability distribution;

2) From $r_{bdp}$, $(x,y)_{bdp}$ are selected uniformly;

3) As with the point source, a tile index is selected. See step 6 in Section IX.C;

4) The sample energy $E_{samp}$ is selected from the tile's associated energy distribution;

5) The sample's z-direction cosine, w, is selected from the tile's "angular" probability distribution;

6) The transverse radial direction cosine, $\cos\phi$, is chosen from the tile's "azimuthal" probability distribution. The x and y direction cosines, (u,v), are then calculated by a rotation of the coordinate system using Equation 13;

$$\sin\theta = \sqrt{1 - w^2} \quad \text{(Eq. 13)}$$
$$u_r = \sin\theta\cos\phi_r$$
$$v_r = \sin\theta\sin\phi_r$$
$$u = (u_r x - v_r y)/r_{bdp}$$
$$v = (v_r x + u_r y)/r_{bdp}$$

7) The assignment of sample weight is easier that with the point source component type. Since the radial position is selected based on an actual distribution, no correction is needed based on position. Also, since we select from the entire defined component, no correction is needed for the sample fraction as with the point source. The sample weight is just $W_{st}/E_{samp}$;

The result is a complete sample description at the BDP with the values (x, y, z, u, v, w, E, W)$_{bdp}$.

IX.E. History File Sampling

The option to use a simulation history file directly has been incorporated into PEREGRINE. This section discusses the technique of generating an internal PEREGRINE particle from a processed history file. See Section VI.F for a discussion on the generation of a processed history file.

The entire file of history events is read into PEREGRINE and stored for subsequent sampling to minimize disk I/O during the Monte Carlo process.

Each history is of the form $(r_{bdp}, u_r, v_a, E)$ at a given $z_{bdp}$. A history is selected by randomly selecting an index into the particle history buffer. After selection, a given history's coordinates are given a random azimuthal rotation of $\phi \epsilon [0, 2\pi)$. The selection of the random rotation angle is done using a standard 2 random number technique: Select $r_1 \epsilon [0,1], r_2 \epsilon [-1,1]$; Reject if $(r_3 = r_1^2 = r_2^2) > 1$; Otherwise, $\cos\phi = 2r_1 r_2/r_3$ and $\sin\phi = (r_2^2 - r_1^2)/r_3$. It is always true that $(\cos\phi)^2 + (\sin\phi)^2 = 1$.

The transformation is given in Equation 14.

$$x_{bdp} = r\cos\phi \quad \text{(Eq. 14)}$$
$$y_{bdp} = r\sin\phi$$
$$u = u_r\cos\phi - v_a\sin\phi$$

-continued $$v = u_r\sin\phi + v_a\cos\phi$$

X. Beam Modifier Tracking Techniques
XA. Jaws
X.A.(i). Point Source Sampling Area Limitation and Integration The subroutine RADINT in PEREGRINE integrates a piecewise constant or piecewise linear radial function over an arbitrary rectangular region to determine the fraction of the function that lies within the rectangle. The purpose is to calculate the correction factor to

X. Beam Modifier Tracking Techniques
XA. Jaws
X.A.(i). Point Source Sampling Area Limitation and Integration The subroutine RADINT in PEREGRINE integrates a piecewise constant or piecewise linear radial function over an arbitrary rectangular region to determine the fraction of the function that lies within the rectangle. The purpose is to calculate the correction factor to the total beam energy necessitated by limiting the sampling region for point sources.

X.A.(ii) Particle/Jaw Intersection
X.A.(iii)a Sloped Face

This first derivation of particle/jaw intersection assumes that the top and bottom planes of a jaw are perpendicular to the beam direction and that the face is sloped to match the ray drawn from the target through the upper jaw corner. Calculation of the straight line path length through such a construct is straightforward. The discussion below concentrates on the jaw set that is perpendicular to the x-z plane. The results are easily converted to the other jaw set by use of the appropriate coordinates (x→y) and direction cosines (u→v).

Figure 6:
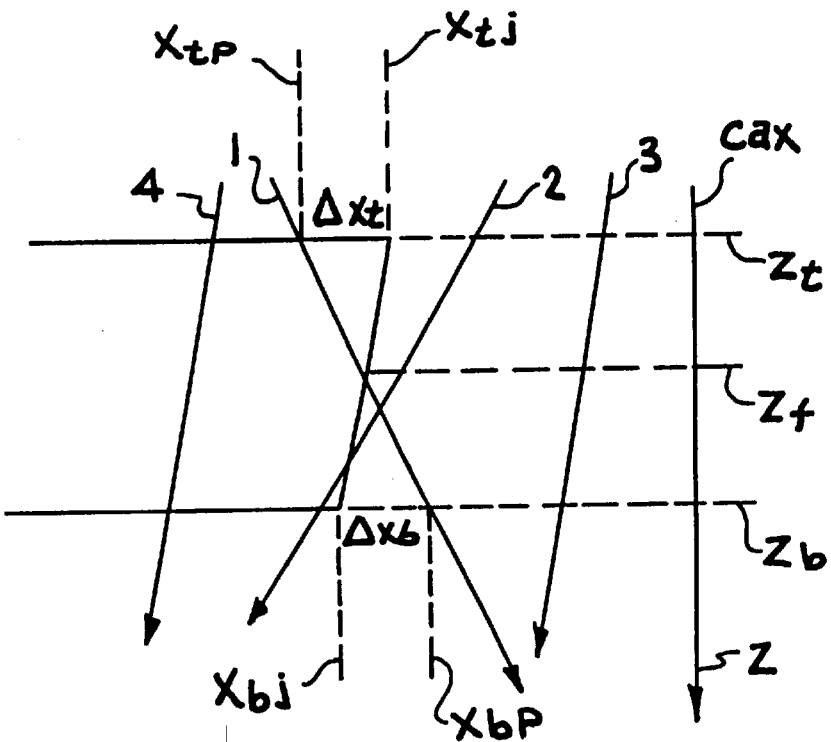
FIG. 6 shows the four cases of a ray passing through the two z-planes that define this model of a jaw.

The four cases of a ray passing through the two z-planes that define this model of a jaw are shown in FIG. 6. The variable needed are shown for the first case: the z locations of the jaw top $z_t$, face intersection $z_f$, and jaw bottom $z_b$; the particle x positions at the jaw top $x_{tp}$ and jaw bottom $x_{bp}$; the top and bottom jaw positions $x_{tj},x_{bj}$; and Case 3) No intersection at all. Both plane penetrations lie in the opening. Here we have $\Delta x_t \Delta x_b > 0$ and $|x_{tj}| > |x_{tp}|$.

Case 4) Full path length. Both crossings are on the jaw. Here we have $\Delta x_t \Delta x_b > 0$ and $|x_{tj}| > |x_{tp}|$. In this case, the attenuation length is $dl_4 = (z_b - z_t)/w$.

For cases 1 and 2, solving for the intersection yields the z location of the intersection of the particle with the jaw face.

$$z_f = z_t + \frac{\Delta x_t (z_b - z_t)}{\Delta x_t - \Delta x_b} \quad \text{(Eq. 15)}$$

Note that the denominator is never zero since the two terms are of opposite sign. It is also clear that $z_t < z_f < z_b$ for z measured from the target.

The path length through the jaw is determined from $\Delta z$ by considering the case. For case 1, the path length through the jaw is $dl = (z_f - z_t)/w$, where w is the z-direction cosine. For case 2, the path length is $dl = (z_b - z_f)/w$.

X.(i)a Rotated Rectangular Jaws

The last step in the above derivation of path length has the approximation that the jaw surfaces (top and bottom) remained perpendicular to the beam axis. This is not true of all machines. It is true, though, of Siemens' jaws. In some cases, the jaws consist of rectangular blocks of metal that pivot to keep their faces tangent to the target ray. The above approximation leads to an underestimate of the path length for case 1 and to an overestimate for case 2. However, it is easy to make a correction to the calculation and get the real path length.

Figure 7:
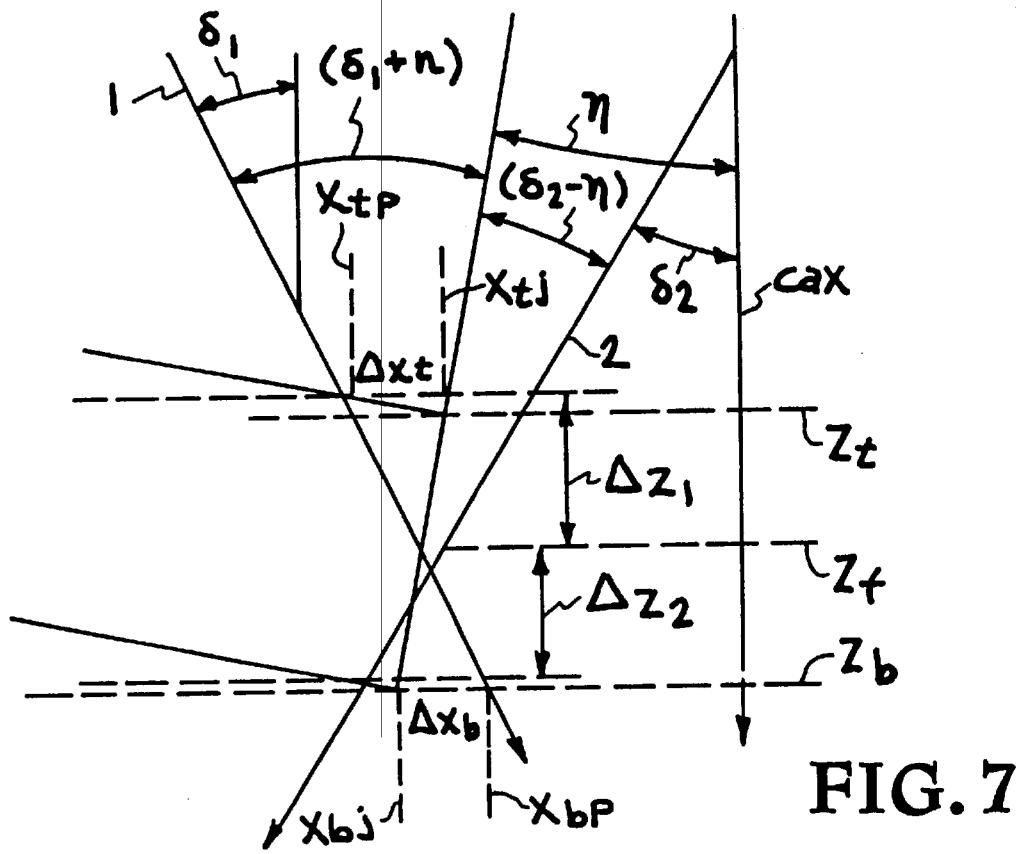
FIG. 7 shows the geometry and additional variables needed for the rotated rectangular jaw.

FIG. 7 shows the geometry and additional variables needed for the rotated rectangular jaw. The coordinate variables retain the same definitions as used in Section X.A(ii). The angles $d_1$ and $d_2$ are defined by the direction of the particle for case 1 and case 2 intersections. For any given sample with direction cosines (u,v,w), $$\tan\delta = u/w \quad \text{(Eq.16)}$$

for the jaws normal to the x direction. Similarly, for the other set of jaws, $\tan\delta = v/w$. The rotation angle h of the jaw is defined by Equation 17.

$$\tan\eta = x_{tj}/z_t \quad \text{(Eq.17)}$$

for rotation about the physical target location at z=0. The other angles are the relative angles between the jaw and the particle's projection on plane normal to the jaw's axis.

Equation 15 can still be used to determine the z location of the face intersection, $z_f$. The path length through the jaw material is $dl = \Delta z/w$. So, what is needed is the z distance through the jaw $\Delta z$. For case 1 intersections, $\Delta_z$ is given by Equation 18.

$$\Delta z_1 = \frac{(z_f - z_t)\cos(\delta_1)}{\cos(\eta)\cos(\delta_1 + \eta)} \quad \text{(Eq. 18)}$$

Simplifying the transcendental functions and using the coordinate based definitions of Equations 16 and 17 results in a formula for $dl_1$ given in Equation 19.

$$dl_1 = \frac{(z_f - z_t)}{w}\left[\frac{1 + (\tan\eta)^2}{1 - \tan\eta\tan\delta}\right] \quad \text{(Eq. 19)}$$

$$= \frac{(z_f - z_t)}{w}\left[\frac{1 + (x_{tj}/z_t)^2}{1 - (x_{tj}u/z_t w)}\right]$$

For case 2 intersections, the only changes are that $(\delta+\eta)$ becomes $(\delta-\eta)$ and $(z_f-z_t)$ becomes $(z_b-z_f)$. The resulting path length $dl_2$ is given by Equation 20.

$$dl_2 = \frac{(z_b - z_f)}{w}\left[\frac{1 + (\tan\eta)^2}{1 - \tan\eta\tan\delta}\right] \quad \text{(Eq. 20)}$$

$$= \frac{(z_b - z_f)}{w}\left[\frac{1 + (x_{tj}/z_t)^2}{1 + (x_{tj}u/z_t w)}\right]$$

It should also be noted that $(z_b-z_f)$ is not the difference between the top and bottom values given in the PEREGRINE machine file for rotating rectangular jaws. If we assume that the upper corner remains at its original z position, then the bottom location $z_b$ moves by a factor of cost. If $T_{jaw}$ is the jaw thickness then $z_b = z_t + T_{jaw}\cos\eta$.

Changes and modifications in the specifically described embodiments can be carried out without departing from the scope of the invention, which is intended to be limited by the scope of the appended claims.

The invention claimed is:

1. A computer implemented process for producing a 3-dimensional map of a radiation dose delivered to a patient, comprising:

constructing patient-dependent information necessary for a Monte-Carlo transport calculation;

executing said Monte-Carlo transport calculation; and producing, from said patient-dependent information and said Monte-Carlo transport calculation, a 3-dimensional map of the dose delivered to said patient, wherein the step of constructing patient dependent-information comprises analyzing Monte Carlo simulation history files of standard linear accelerators and generating compact, 9 dimensional probability distribution functions (PDFs) describing a patient-independent radiation field for use in said Monte Carlo dose calculation, wherein said 9 dimensional PDFs comprise 7 degrees of freedom, wherein memory storage requirements are reduced and subsequent calculations to select an arbitrary number of uncorrelated samples from the PDF are allowed.

2. The computer implemented process of claim 1, wherein said 7 degrees of freedom comprise:

spectral energy;

energy fluence (sample weight);

two positional degrees of freedom, comprising:
radius on beam definition plane (BDP); and
radius on virtual source plane (VSP);

an angular degree of freedom;

radiation type (discrete); and component of origin (discrete).

3. The computer implemented process of claim 2, wherein said angular degree of freedom comprises azimuthal angle on VSP, wherein said radiation type (discrete) comprises photon (x-ray), electron, neutron and proton radiation; and wherein said component of origin (discrete) comprises E.G.: target, flattening filter, primary collimator.

4. The computer implemented process of claim 1, wherein the step of constructing patient dependent-information further comprises including in the analysis the eventual effects of some patient-dependent beam modifiers to provide data necessary for highly efficient sampling.

5. The computer implemented process of claim 1, wherein the step of constructing patient dependent-information further comprises precalculating the effects of collimator jaws on the shadowing of the beam definition plane to eliminate large portions of PDF from consideration at run time.

6. The computer implemented process of claim 1, wherein the step of constructing patient dependent-information further comprises assembling a treatment device description (TDD) from a radiation field PDF and from engineering details of the patient dependent beam modifiers specific to each clinical installation.

7. The computer implemented process of claim 1, wherein the step of constructing patient dependent-information further comprises adjusting the PDFs using linear parameters and clinical measurements to give absolute calibration of the radiation field for each clinical installation.

8. The computer implemented process of claim 7, wherein said linear parameters comprise:

a global monitor unit factor comprising a global normalization constant that defines the dose/MU for a 40×40 field;

a monitor chamber parameter, radius and position, to adjust said monitor unit factor to account for deviations in calculated output factors from the measured values;

a global and radial energy scale factor comprising multipliers on the energy axis of beam-definition-plane energy spectra; and a radial fluence scale factor comprising a multiplier on the energy fluence that is proportional to the radius on the beam definition plane.

9. The computer implemented process of claim 1, wherein the step of constructing patient dependent-information further comprises storage, access and maintenance routines for use in calibration and dose calculation.

10. The computer implemented process of claim 1, wherein the step of constructing patient dependent-information further comprises sampling methods for efficiently selecting random samples that accurately reproduce the original simulations (for unadjusted PDFs) or the actual radiation fields used in treatment (for adjusted PDFs).

11. The computer implemented process of claim 10, wherein said sampling methods are extensible to any radiation beam type.

12. The computer implemented process of claim 11, wherein said radiation beam type is selected from a group consisting of x-rays, electrons, protons, neutron and heavy ions.

13. The computer implemented process of claim 12, wherein said radiation beam type can be mixed in a single TDD to account for radiation field contamination (such as electrons in an x-ray beam (or vice versa), or neutrons in a proton beam).

14. The computer implemented process of claim 1, wherein the step of constructing patient dependent-information further comprises formats and access to the clinical data used in calibration for quality assurance.

* * * * *